US012569183B2

(12) United States Patent
Ivaturi et al.

(10) Patent No.: US 12,569,183 B2
(45) Date of Patent: *Mar. 10, 2026

(54) METHOD OF ADMINISTERING SOTALOL IV/SWITCH

(71) Applicant: University Of Maryland, Baltimore, Baltimore, MD (US)

(72) Inventors: Vijay Ivaturi, Baltimore, MD (US); Jogarao Gobburu, Herndon, VA (US)

(73) Assignee: University Of Maryland, Baltimore, Baltimore, MD (US)

( * ) Notice: Subject to any disclaimer, the term of this patent is extended or adjusted under 35 U.S.C. 154(b) by 653 days.

This patent is subject to a terminal disclaimer.

(21) Appl. No.: 18/156,092

(22) Filed: Jan. 18, 2023

(65) Prior Publication Data

US 2023/0225664 A1     Jul. 20, 2023

Related U.S. Application Data

(63) Continuation of application No. 17/003,297, filed on Aug. 26, 2020, now Pat. No. 11,583,216, which is a continuation of application No. 16/376,706, filed on Apr. 5, 2019, now Pat. No. 10,799,138.

(60) Provisional application No. 62/652,943, filed on Apr. 5, 2018.

(51) Int. Cl.

| | |
|---|---|
| *A61B 5/361* | (2021.01) |
| *A61B 5/00* | (2006.01) |
| *A61B 5/349* | (2021.01) |
| *A61K 9/00* | (2006.01) |
| *A61K 31/18* | (2006.01) |
| *G16H 20/17* | (2018.01) |
| *G16H 50/20* | (2018.01) |
| *G16H 50/30* | (2018.01) |

(52) U.S. Cl.
CPC .............. *A61B 5/361* (2021.01); *A61B 5/349* (2021.01); *A61B 5/4839* (2013.01); *A61K 9/0019* (2013.01); *A61K 9/0053* (2013.01); *A61K 31/18* (2013.01); *G16H 20/17* (2018.01); *G16H 50/20* (2018.01); *G16H 50/30* (2018.01)

(58) Field of Classification Search
CPC .... A61B 5/361; A61K 9/0019; A61K 9/0053; A61K 31/18
See application file for complete search history.

(56) References Cited

U.S. PATENT DOCUMENTS

| | | | |
|---|---|---|---|
| 6,043,273 | A | 3/2000 | Duhaylongsod |
| 6,060,454 | A | 5/2000 | Duhaylongsod |
| 6,101,412 | A | 8/2000 | Duhaylongsod |
| 6,136,327 | A | 10/2000 | Gupta et al. |
| 6,281,246 | B2 | 8/2001 | Sankaranarayanan |
| 6,369,114 | B1 | 4/2002 | Weil et al. |
| 6,482,811 | B1 | 11/2002 | Bacaner et al. |
| 6,491,039 | B1 | 12/2002 | Dobak, III |
| 6,500,459 | B1 | 12/2002 | Chhabra et al. |
| 6,627,223 | B2 | 9/2003 | Percel et al. |
| 6,632,217 | B2 | 10/2003 | Harper et al. |
| 6,720,001 | B2 | 4/2004 | Chen et al. |
| 6,800,668 | B1 | 10/2004 | Odidi et al. |
| 6,899,700 | B2 | 5/2005 | Gehling et al. |
| 7,004,171 | B2 | 2/2006 | Benita et al. |
| 7,005,425 | B2 | 2/2006 | Belardinelli et al. |
| 7,022,343 | B2 | 4/2006 | Philbrook et al. |
| 7,048,945 | B2 | 5/2006 | Percel et al. |
| 7,090,830 | B2 | 8/2006 | Hale et al. |
| 7,179,597 | B2 | 2/2007 | Woosley |
| 7,341,737 | B2 | 3/2008 | Gehling et al. |
| 7,371,254 | B2 | 5/2008 | Dobak, III |
| 7,417,038 | B1 | 8/2008 | Anker et al. |
| 7,526,335 | B2 | 4/2009 | Ferek-Petric |
| 7,538,092 | B2 | 5/2009 | Orlando et al. |
| 7,815,936 | B2 | 10/2010 | Hasenzahl et al. |
| 7,829,573 | B2 | 11/2010 | Curwen et al. |
| 7,951,183 | B2 | 5/2011 | Dobak, III |
| 8,263,125 | B2 | 9/2012 | Vaya et al. |
| 8,268,352 | B2 | 9/2012 | Vaya et al. |
| 8,313,757 | B2 | 11/2012 | Van Lengerich |
| 8,377,994 | B2 | 2/2013 | Gray et al. |
| 8,399,018 | B2 | 3/2013 | Lichter et al. |
| 8,440,168 | B2 | 5/2013 | Yang et al. |
| 8,465,769 | B2 | 6/2013 | Petereit et al. |
| 8,466,277 | B2 | 6/2013 | Orlando et al. |
| 8,696,696 | B2 | 4/2014 | Solem |
| 8,709,076 | B1 | 4/2014 | Matheny et al. |
| 8,753,674 | B2 | 6/2014 | Helson |
| 8,828,432 | B2 | 9/2014 | Van Lengerich |
| 8,865,213 | B2 | 10/2014 | Sheth et al. |
| 8,871,452 | B2 | 10/2014 | Lee |
| 8,906,847 | B2 | 12/2014 | Cleemann et al. |
| 8,987,262 | B2 | 3/2015 | Leaute-Labreze et al. |

(Continued)

OTHER PUBLICATIONS

J. Somberg et al. Cardiology 2010;116:219-225. (Year: 2010).*

(Continued)

*Primary Examiner* — James H Alstrum-Acevedo
*Assistant Examiner* — Manahil Mirghani Ali Abdalhameed
(74) *Attorney, Agent, or Firm* — Wolter Van Dyke Davis, PLLC; Eugene J. Molinelli; Martha Cassidy

(57) ABSTRACT

Embodiments of the invention are broadly drawn to methods for determining an optimum dose of an antiarrhythmic drug, for example sotalol. In particular, the method involves titrating the dose of the drug gradually to determine the optimum plasma concentration for a patient, whether the patient has normal or abnormal renal function.

23 Claims, 10 Drawing Sheets

(56) References Cited

U.S. PATENT DOCUMENTS

| | | | |
|---|---|---|---|
| 9,011,526 B2 | 4/2015 | Matheny | |
| 9,044,319 B2 | 6/2015 | Matheny | |
| 9,060,969 B2 | 6/2015 | Matheny | |
| 9,078,929 B2 | 7/2015 | Kuebelbeck et al. | |
| 9,161,952 B2 | 10/2015 | Matheny et al. | |
| 9,239,333 B2 | 1/2016 | Snider | |
| 9,308,084 B2 | 4/2016 | Matheny | |
| 9,474,719 B2 | 10/2016 | Mullen et al. | |
| 9,554,989 B2 | 1/2017 | Kaplan et al. | |
| 9,585,851 B2 | 3/2017 | Yun et al. | |
| 9,616,026 B2 | 4/2017 | Singh | |
| 9,682,041 B2 | 6/2017 | Helson | |
| 9,724,297 B2 | 8/2017 | Thomas et al. | |
| 2007/0009654 A1 | 1/2007 | Watanabe et al. | |
| 2014/0235631 A1 | 8/2014 | Bunt et al. | |
| 2014/0276404 A1 | 9/2014 | Orlowski | |
| 2015/0081010 A1 | 3/2015 | Matheny | |
| 2015/0210712 A1 | 7/2015 | Blumberg et al. | |
| 2016/0082159 A1 | 3/2016 | Orlowski | |
| 2016/0128944 A1 | 5/2016 | Chawrai et al. | |
| 2016/0228379 A1 | 8/2016 | Kumar et al. | |
| 2016/0271070 A1 | 9/2016 | Singh et al. | |
| 2016/0271157 A1 | 9/2016 | Ahmed et al. | |
| 2016/0303133 A1 | 10/2016 | Dudley et al. | |
| 2016/0317388 A1 | 11/2016 | Bhargava et al. | |
| 2017/0049705 A1 | 2/2017 | Mateescu et al. | |
| 2017/0100387 A1 | 4/2017 | Arora et al. | |
| 2017/0119627 A1 | 5/2017 | Bhargava et al. | |
| 2017/0157076 A1 | 6/2017 | Yacoby-Zeevi et al. | |
| 2017/0231885 A1 | 8/2017 | Cremers et al. | |
| 2017/0296493 A1 | 10/2017 | Thomas et al. | |
| 2017/0348303 A1 | 12/2017 | Bosse et al. | |
| 2018/0071390 A1 | 3/2018 | Patel et al. | |

OTHER PUBLICATIONS

Brendorp, B. et al. Drug-Safety 25, 847-865 (2002). (Year: 2002).*
Patel P, Goyal A. Antiarrhythmic Medications. [Updated Feb. 28, 2024]. In: StatPearls [Internet]. Treasure Island (FL): StatPearls Publishing; Jan. 2025—. Available from: ncbi.nlm.nih.gov/books/NBK482322/. (Year: 2025).*
Amiodarone HCI Injection for intravenous use, Novaplus (Registered), 4 pages.
Barbey, J.T., et al., "Pharmacokinetic, ptiarmacodynamic, and safety evaluation of an accelerated dose titration regimen of sotalol in healthy middle-aged subjects", "Clinical Pharmacology Therapeutics", Jul. 1999, pp. 91-99, vol. 66, No. 1, Publisher: Mosby, Inc., Published in United States.
Batul, SA, et al., "Intravenous Sotalol—Reintroducing a Forgotten Agent to the Electrophysiology Therapeutic Arsenal", "Journal of Atrial Fibrillation", Feb. 2017, pp. 1-5, vol. 9, No. 5, Publisher: Cardiotext Publishing, Published in: United States.
Cordarone (Registered) (amiodarone HCI) Tablets, NDA 18-972/S-038/039, 29 pages.
El-Assaad, I., et al., "Lone Pediatric Atrial Fibrillation in the United States: Analysis of Over 1500 Cases", "Pediatr. Cardiol", Apr. 3, 2017, pp. 1004-1009, vol. 38, Publisher: Springer Publishing, Published in: DOI 10.1007/s00246-017-1608-7.
FDA "Highlights of Prescribing Information sotalol hydrochloride injection," 2009 https://www.accessdata.fda.gov/drugsatfda_docs/label/2009/022306s000lbl.pdf (Year: 2009).
FDA Highlights of Prescribing Information Sotylize (sotalol hydrochloride), 2014 https://www.accessdata.fda.gov/drugsatfda_docs/label/2014/205108s000lbl.pdf (Year: 2014).
Flecainide Acetate—flecainide tablet, Ranbaxy Pharmaceuticals Inc., 17 pages.
Galloway, C., et al., "Development and Validation of a Deep-Learning Model to Screen for Hyperkalernia From tile Electrocardiogram", "JAMA Cardiology", Apr. 3, 2019, pp. E1-E9, Publisher: American Medical Association, Publislled in: doi:10.1001/jamacardio.2019.0640.

Hannun, A.Y., et al., "Cardiologist-level arrhythmia detection and classification in ambulatory electrocardiograms using a deep neural network", "Nature Medicine", Jan. 2019, pp. 65-69, vol. 25, Publisher: Nature Publishing, Published in: https://doi.org/10.1038/s41591-018-0268-3.
Ho, O.S.W., et al., "Rapid intravenous infusion of d-i sotalol: time to onset of effects on ventricular refractoriness, and safety", "European Heart Journal", 1995, pp. 81-86, vol. 16, Publisher The European Society of Cardiology, Published in: DOI: 10.1093/eurheartj/16.1.81.
Ibutilide Fumarate—ibutilide fumarate injection, solution, Mylan Institutional LLC, 2021, 14 pages.
Laer, S., et al., "Development of a safe and effective pediatric dosing regimen for sotalol based on population pharmacokinetics and pharmacodynamics in children with supraventricular tachycardia", "J. American College of Cardiology", Oct. 14, 2005, pp. 1322-1330, vol. 46, No. 7, Publisher: Elsevier, inc., Published in: doi:10,1016/j.jacc.2005.06,061.
Learn the Heart "Antiarrhythmic Drug Review," https://www.healio.com/cardiology/learn-the-heart/cardiology-review/topic-reviews/antiarrhythmic-drugs (Year: 2022).
Li, X., et al., "Efficacy of Intravenous Sotalol for Treatment of Incessant Tachyarrhythmias in Children", "The American Journal of Cardiology", May 2017, pp. 1366-1370, vol. 119, No. 9, Publisher: Elsevier, Inc., Published in: https://doi.org/10.1016/j.amjcard.2017.01,034.
Lynch, J. J., et al., "Prevention of ventricular fibrillation by dextrorotatory sotalol in a conscious canine model of sudden coronary death", "American Heart Journal", May 1985, pp. 949-958, vol. 109, No. 5, Publisher: Elsevier, Inc., Published in: United States.
Marill, K. A, et al.,, "Meta-analysis of the Risk of Torsades de Pointes in Patients Treated with Intravenous Racemic Sotalol", "Academic Emergency Medicine", Feb. 2001, pp. 117-124, vol. 8, No. 2, Publisher: Wiley, Published in: United States.
Multaq (dronedarone), Warning: Increased risk of Death, Stroke and Heart Failure Inpatients With decompensated Heart failure or Permanent atrial Fibrillation, Highlights Of prescribing information, 2009, 24 pages.
Neumar, RW., et al., "Part 8: Adult Advanced Cardiovascular Life Support", "Circulation", Nov. 2, 2010, pp. S729-S767, vol. 122, No. 3, Publisher: American Heart Association Journals, Published in: DOI: 10.1161/CIRCULATIONAHA.110.970988.
Peters, F.P.J,, et al., "Treatment of recent onset atrial fibrillation with intravenous solalol and/or flecainide", "Netherlands Journal of Medicine", Apr. 28, 1998, pp. 93-96, vol. 53, Publisher: Elsevier Science B. V., Published in: Netherlands.
Procainamide Dosage, Drugs.com., 2021, 3 pages.
Procainamide Hydrochloride—procainamide hydrochloride injection, solution, Hospira, Inc., 2021, 12 pages.
Radford, D,J., et al, "Atrial Fibrillation in Children", "Pediatrics", Feb. 1977, pp. 250-256, vol. 59, No. 2, Publisher: American Academy of Pediatrics, Published in: United States.
Rythmol, (propafenone hydrochloride tablets), for oral use Highlights of Prescribing Information, 1989, 24 pages.
Saul, J.P., et al., "Pharmacokinetics and pharmacodynamics of sotaiol in a pediatric population with supraventricular and ventricular tachyarrhythmia", "Clinical Pharmacology & Therapeutics", Mar. 2001, pp. 145-157, vol. 69, Publisher: Mosby, Inc,, Published in: doi:10.1067/mcp.2001.113795.
Snider, M., et al., "Initiai experience with antiarrhythmic medication monitoring by clinical pharmacists in an outpatient setting: a retrospective review", "Clinical Therapeutics", Jun. 2009, pp. 1209-1218, vol. 31, No. 6, Publisher: Excerpta Medica, Inc., Published in: doi:10.1016/j.clinthera.2009.06.014.
Somberg, J.C., et al., "Developing a Safe Intravenous Sotalol Dosing Regimen", "American Journal of Therapeutics", 2010, pp. 365-372, vol. 17, No. 4, Publisher: Lippincott Williams & Wilkins, Published in: United States.
Somberg; JC.; et al., "Gender Differences in Cardiac Repolarization Following Intravenous Sotalol Administration", "Journal of Cardiovascular Pharmacology and Therapeutics", 2012, pp. 86-92, vol. 17, No. 1, Publisher: Sage, Published in: DOI: 10.1177/1074248411406505.

(56) References Cited

OTHER PUBLICATIONS

Someberg et al. "QT prolongation and serum sotalol concentration are highly correlated following intravenous and oral sotalol," Cardiology, 2010, vol. 116, pp. 219-225. (Year: 2010).

Sotalol hydrochloride injection for interavenous use, Highlights of prescribing information, 2009, 11 pages.

Sotalol Hydrochloride injection, for intravenous use, Highlights of precribng information, 2020, 16 pages.

Sotylize (sotalol hydrochloride) oral solution, Highlights of precribing information, 2014, 19 pages.

Thomas, SP., et al., "Rapid loading of sotalol or amiodarone for management of recent onset symptomatic atrial fibrillation: A randomized, digoxin-controlled trial", "American Heart Journal", Jan. 2004, pp. 1-6, vol. 147, No. 1, Publisher: Elsevier, Inc., Published in: doi:10.1016/S0002-8703(03)00526-X.

Tikosyn (Registered) (dofetilide) Capsules, Reference ID: 4474154, 30 pages.

Valdes, S.O., et al., "Early experience with intravenous sotalol in children wittl and without congenital heart disease;,, Heart Rhythm", Dec. 2018, pp. 1862-1869, vol. 15, No. 12, Publisher: Elsevier Inc., Published in: https://doi.org/10.1016/j.hrthm.2018.07.010.

Yarlagadda, B., et al., "Safety and Efficacy of Inpatient Initiation of Dofetilide Versus Sotaiol for Atrial Fibrillation", "Journal of Atrial Fibrillation", Dec. 2017, pp. 1-5, vol. 10, No. 4, Published in: doi: 10.4022/jafib.1805.

* cited by examiner

FIG. 1B

| Pharmacokinetic model parameter estimates | | | |
|---|---|---|---|
| Parameter | Units | Estimate | BSV (%) |
| Clearance | L/hr/70kg | 12 | 14 |
| Central Volume of Distribution | L/70kg | 77.1 | 26.7 |
| Distribution clearance | L/hr/70kg | 9.22 | |
| Peripheral Volume of Distribution | L/70kg | 52.3 | |
| Absorption Rate Constant | 1/hr | 0.605 | 68.5 |
| Lag time of absorption | hr | 0.231 | |
| Baseline QTc | msec | 405 | 15.8 |
| Concentration-QTc Slope | | 0.0158 | 58.3 |
| RUVpk-proportional | %CV | 47.5 | |
| RUVqtc-additive | msec | 19.1 | |
| BSV – Between subject variability | | | |
| RUV – Residual unexplained variability | | | |

| Prior Stable Dose (mg) | IV Loading Dose (mg) | Infusion Time (hr) | Maintenance Dose Initiation |
|---|---|---|---|
| 80 | 20, 30, 40, 50, 60, 70, 75,80 | 1, 2, 3 | End of infusion, 12 hours after end of infusion |

FIG. 6

| Sotalol dosing regimens using and IV/PO switch strategy to reach Cmax,ss in patients that need to be re-stabilized on prior stable dose | | | |
|---|---|---|---|
| Target Oral Maintenance Dose | Proposed Dosing Regimen [Dose + Duration of Infusion] To Reach Cmax,ss | Time of Administering 2nd Oral Dose | Time to Cmax,ss |
| 80 mg BID | 40 mg IV sotalol infusion administered over 2 hours + 80 mg PO immediately at the end of 2 hour infusion | 12 hours after $T_{0 \text{ hours}}$  All subsequent doses should be given 12 hours apart. | Cmax,ss achieved after 4 hours of initiating the loading infusion (i.e. 4 hours after $T_{0 \text{ hours}}$). |
| 120 mg BID | 60 mg IV sotalol infusion administered over 2 hours + 120 mg PO immediately at the end of 2 hour infusion | Renal Impairment 24 hours after $T_{0 \text{ hours}}$  All subsequent doses should be given 24 hours apart. | |
| 160 mg BID | 80 mg sotalol infusion administered over 2 hours + 160 mg PO immediately at the end of 2 hour infusion | | |

FIG. 7

| Sotalol dosing regimens using IV/IV switch strategy to reach Cmax,ss in patients that need to be re-stabilized on prior stable dose | | |
|---|---|---|
| Proposed Dosing Regimen [Dose + Duration of Infusion] To Reach Cmax,ss | Time of Administering 2nd IV Dose | Time to Cmax,ss |
| 40 mg IV sotalol infusion administered over 2 hours + 75 mg IV immediately at the end of 2 hour infusion | 12 hours after $T_{0\,hours}$<br><br>All subsequent doses should be given 12 hours apart.<br><br>Renal Impairment<br>24 hours after $T_{0\,hours}$<br><br>All subsequent doses should be given 24 hours apart. | Cmax,ss achieved after 7 hours of initiating the loading infusion (i.e. 7 hours after $T_{0\,hours}$). |

FIG. 8

| Titration dosing regimens to reach Cmax,ss in sotalol-naïve patients using a IV/PO switch strategy | | | |
|---|---|---|---|
| Target Oral Maintenance Dose | Normal Renal Function | Renal Impairment | |
| | Proposed Titration Design [Dose + Duration of Infusion] To Reach Cmax,ss | Proposed Titration Design [Dose + Duration of Infusion] To Reach Cmax,ss | Escalation Plan |
| REG 1 80 mg BID | 40 mg IV sotalol infusion administered over 1 hour + 80 mg PO at 2 hours from start of infusion + BID PO from 12 hours | 40 mg IV sotalol infusion administered over 1 hour + 80 mg PO at 2 hours from start of infusion + QD PO from 24 hours | Measure QT, at end of 1 hour (1 infusion) • If delta QT acceptable – proceed to REG2 • If delta QT is high – stay with REG1 under monitoring |
| REG 2 120 mg BID | 40 mg IV sotalol infusion administered over 1 hours + 20 mg IV sotalol infusion administered over 0.5 hour + 120 mg PO at 2 hours from start of infusion + BID PO from 12 hours | 40 mg IV sotalol infusion administered over 1 hours + 10 mg IV sotalol infusion administered over 0.5 hour + 120 mg PO at 2 hours from start of infusion + QD PO from 24 hours | Measure QT$_c$ at end of 1.5 hours (2 infusions) • If delta QTc acceptable – proceed to REG3 • If delta QT is high – stay with REG2 under monitoring or de-escalate to REG1 |
| REG 3 160 mg BID | 40 mg sotalol infusion administered over 1 hour + 20 mg infusion administered over 0.5 hour + 20 mg infusion administered over 0.5 hour + 160 mg PO at 2 hours from start of infusion + BID PO from 12 hours | 40 mg sotalol infusion administered over 1 hour + 20 mg infusion administered over 0.5 hour + 10 mg infusion administered over 0.5 hour + 160 mg PO at 2 hours from start of infusion + QD PO from 24 hours | Measure QT$_c$ at end of 2 hours (3 infusions) • If delta QT acceptable – switch to REG3 • If delta QTc is high – stay with REG3 under monitoring or de-escalate to REG2 or REG1 |

METHOD OF ADMINISTERING SOTALOL IV/SWITCH

CROSS-REFERENCE TO RELATED APPLICATIONS

This application is a continuation of U.S. patent application Ser. No. 17/003,297, filed 26 Aug. 2020, which is a continuation of U.S. patent application Ser. No. 16/376,706, filed 5 Apr. 2019 (now U.S. Pat. No. 10,799,138), which claims the benefit of U.S. Provisional Application No. 62/652,943, filed Apr. 5, 2018. The entirety of these patent documents is incorporated herein.

BACKGROUND OF THE INVENTION

Congenital long-QT syndrome is a genetic disorder encompassing a family of mutations that can lead to aberrant ventricular electrical activity. These genetic mutations are called "channelopathies"; they are the responsible genes that encode for protein channels that regulate the flow of sodium, potassium, and calcium ions in and out of the cardiac myocyte. The result of these mutations is an increased risk of ventricular arrhythmia, specifically torsade de pointes that can lead to syncope, aborted cardiac arrest, and sudden cardiac death. Acquired long-QT and secondary arrhythmias can result from cardiac ischemia, bradycardia and metabolic abnormalities such as low serum potassium or calcium concentration.

Acquired long-QT can also result from treatment with certain medications, including antibiotics, antihistamines, general anesthetics, and, most commonly, antiarrhythmic medications. (Zipes D P, *Am. J. Cardiol*. v59, pp6E-31E, 1987). Indeed, many promising drugs for treating a plethora of different diseases have been abandoned in the early stages of drug testing because of adverse side effects related to causing acquired long-QT.

Cardiac arrhythmias are a common cause of morbidity and mortality, accounting for approximately 11% of all natural deaths (e.g., see Kannel W B, Kannel C, Paffenbarger R S Jr, Cupples L A., "Heart rate and cardiovascular mortality: the Framingham Study" Am Heart J. v113, no. 6, pp1489-94, June 1987, hereinafter *Kannel* 1987; and Willich S N, Stone P H, Muller J E, Tofler G H, Crowder J, Parker C, Rutherford J D, Turi Z G, Robertson T, Passamani E, et al., "High-risk subgroups of patients with non-Q wave myocardial infarction based on direction and severity of ST segment deviation," *Am Heart J*, v114, no. 5, pp1110-9, November 1987, hereinafter Willich 1987). In general, presymptomatic diagnosis and treatment of individuals with life-threatening ventricular tachyarrhythmias is poor; and, in some cases, medical management actually increases the risk of arrhythmia and death (Cardiac Arrhythmia Suppression Trial II Investigators, 1992). These factors make early detection of individuals at risk for cardiac arrhythmias and arrhythmia prevention high priorities.

Although long-QT (LQT) is not a common diagnosis, ventricular arrhythmias are very common; more than 300,000 United States citizens die suddenly every year (Kannel 1987; Willich 1987) and, in many cases, the underlying mechanism may be aberrant cardiac re-polarization.

Atrial fibrillation (AF) is a type of cardiac arrythmia that can lead to blood clots, stroke, heart failure and other related complications. At least 2.7 million Americas live with AF. Pharmacological control of atrial fibrillation (AF) can be achieved with class III antiarrhythmic drugs (AADs) such as sotalol, amiodarone or dofetilide. Sotalol can be used intravenously or orally. For intravenous (IV) use, sotalol is an antiarrhythmic agent, and for oral use sotalol is for maintenance of normal sinus rhythm, such as for patients that have a history of normal symptomatic atrial fibrillation or flutter. The FDA mandates in-hospital initiation of sotalol, especially for patients with co-morbid diseases, to reduce the risk of adverse events (AE) such as QTc-related torsades de pointes (See Kim, 2011). In addition to maintenance of normal sinus rhythm in patients with symptomatic atrial fibrillation or atrial flutter (AF/AFL), oral sotalol is used in the acute management of life-threatening ventricular arrhythmias as recommended by the Advanced Cardiovascular Life Support (ACLS) clinical guidelines (Neumar, 2010).

For a patient's heart electrical cycle, a QT interval (QT) is a time measured between a beginning of a Q wave and an end of a following T wave. Since the QT can be affected by a patient's heart rate, the QT can be corrected (QTc) to a baseline heart-rate corrected interval based on many factors, such as electrolyte abnormalities, a diurnal effect, autonomic fluctuations, ECG variability, and the like.

In AF treatment, oral (PO) sotalol is recommended to be initiated at a dose of 80 mg twice daily, with gradual titration to 240 and 360 mg/day as needed (e.g., oral sotalol USPI). Intravenous sotalol, a relatively newer addition to the market, and is used as an alternative to PO therapy in patients unable to take oral sotalol (e.g., US Prescribing Information for sotalol hydrochloride injection). The bioavailability of oral sotalol is close to 100% compared to the IV sotalol. Each dose of IV sotalol is administered as a 5-hour infusion to mimic the pharmacokinetics of oral therapy. A boxed warning for both products recommends that treatment be initiated in a hospital setting that facilitates QTc monitoring until steady-state exposures are achieved on day 3, after 4-5 doses of sotalol administered twice daily. The three-day hospital stay can be a major inconvenience for healthcare professionals and patients alike and may significantly increase the cost burden associated with length of stay.

SUMMARY OF THE INVENTION

In embodiments described herein, a method including detecting a baseline QTc of a subject, administering a first dose of an antiarrhythmic drug via a first intravenous infusion for first duration of time, then determining the difference between the baseline QTc and a first QTc measured after the first intravenous infusion to detect a first delta QTc. The method further includes if the first delta QTc detected is in an acceptable range of less than 20% from the baseline, then administering a second dose of the antiarrhythmic drug via a second intravenous infusion for a second duration of time. If the first delta QTc is not acceptable, then discontinuing intravenous administration and administering any further doses of the drug orally.

In other embodiments, a method including administering a first dose of an antiarrhythmic drug to a patient via a first intravenous infusion, infused for a 0.5 hour-2 hour time period, and administering a second dose of the drug via a second intravenous infusion upon completion of the first intravenous infusion is provided herein.

BRIEF SUMMARY OF THE DRAWINGS

The present invention is illustrated by way of example, and not by way of limitation, in the figures of the accompanying drawings and in which like reference numerals refer to similar elements and in which:

FIG. 1B is a table of pharmacokinetic model parameter estimates.

FIG. 6 is a table of Sotalol dosing regimens using and IV/PO switch method to reach Cmax,ss in patients that need to be re-stabilized on prior stable dose.

FIG. 7 is a table of Sotalol dosing regimens using and IV/IV switch method to reach Cmax,ss in patients that need to be re-stabilized on prior stable dose.

FIG. 8 is a table of a titration dosing regimens to reach Cmax,ss in sotalol-naïve patients using a IV/PO switch method.

DETAILED DESCRIPTION

Figure 1A:
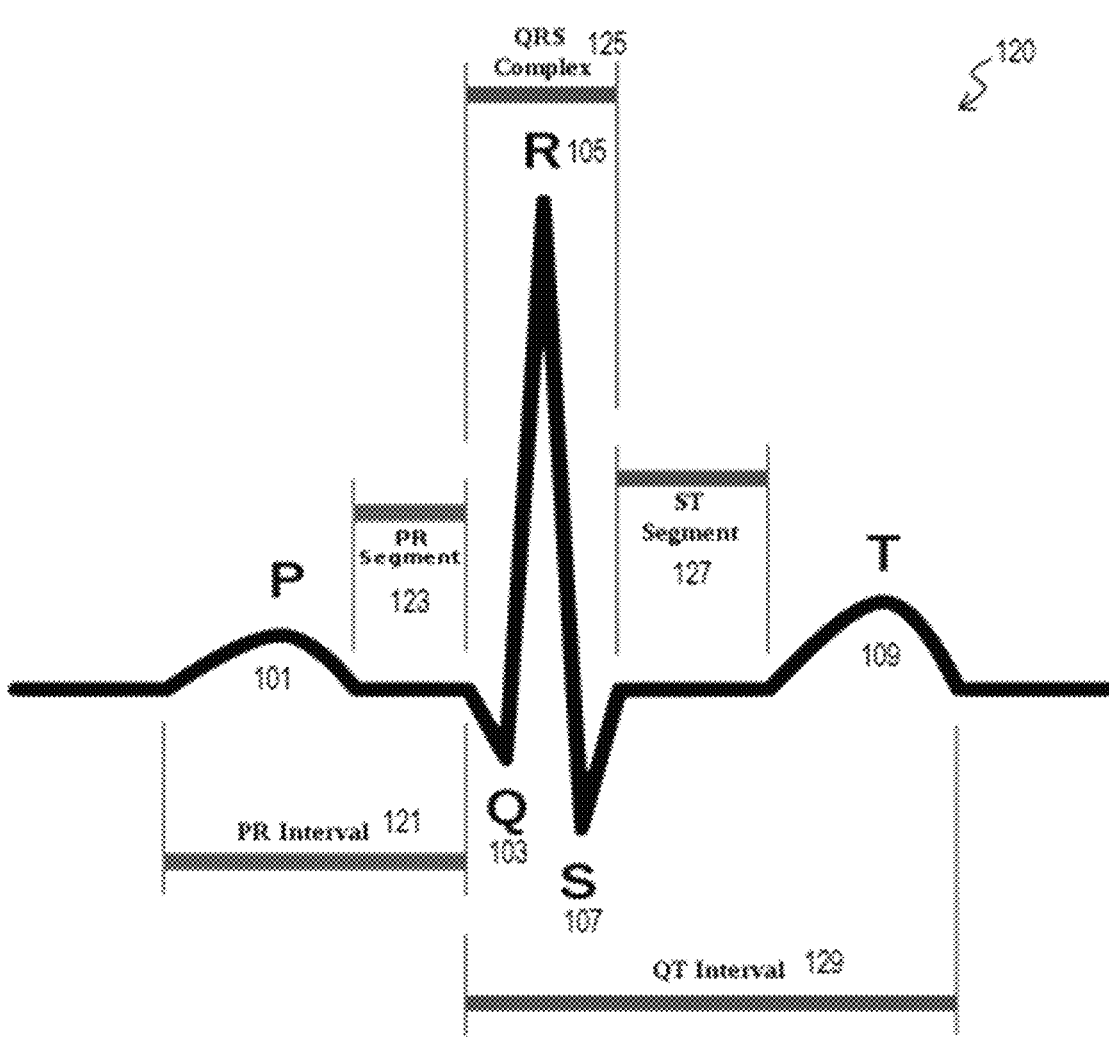
FIG. 1A is a block diagram that illustrates an example ECG according to an embodiment.

Embodiments of the invention are broadly drawn to methods for determining an optimum dose of an antiarrhythmic drug, for example sotalol, to be administered to a subject to treat atrial fibrillation. In particular, the method involves titrating the dose of the drug gradually to determine the optimum plasma concentration for a patient, whether the patient has normal or abnormal renal function.

Methods are described for dosing the antiarrhythmic drug for accelerating achievement of steady-state maximum plasma concentration (Cmax,ss) of the therapeutic agent by intravenous administration or a combination of intravenous and oral administration. The therapeutic agent may include sotalol for treating serious abnormal heart rhythms. In the following description, for the purposes of explanation, numerous specific details are set forth in order to provide a thorough understanding of the present invention. It will be apparent, however, to one skilled in the art that the present invention may be practiced without these specific details. Various references are cited below. In each case the cited reference is hereby incorporated in its entirety as if fully set forth herein, except for terminology inconsistent with that used herein.

The following terms as used herein have the corresponding meanings given here.

TABLE 1

| | Definitions of terms used herein |
|---|---|
| LQT | Long-QT syndrome, a condition in which the duration of time betweenthe onset of the QRS complex and the termination of the T wave on the electrocardiogram (ECG) is prolonged. LQT is a risk marker for a heightened propensity for the occurrence of specific heart beat arrhythmias. |
| subject | An organism that is an object of a method or material, including mammals, e.g., humans, dogs, cows, horses, kangaroos, pigs, sheep, goats, cats, mice, rabbits, rats, and transgenic non-human animals. Synonyms used herein include "patient" and "animal" |
| antiarrhythmic drug (AAD) | A drug within a class of drugs used to treat abnormal heart rhythms, or arrythmias. |
| therapeutically effective amount | an amount of a therapeutic agent, which achieves an intended therapeutic effect in a subject, e.g., eliminating or reducing the severity of a disease or set of one or more symptoms The full therapeutic effect does not necessarily occur by administration of one dose and may occur only after administration of a series of doses. Thus, a therapeutically effective amount may be administered in one or more |
| treating | taking steps to obtain beneficial or desired results, including clinical results, such as alleviating or ameliorating one or more symptoms of a disease; diminishing the extent of disease; delaying or slowing disease progression; ameliorating and palliating or stabilizing a metric (statistic) of disease. "Treatment" refers to the steps taken. |
| naive | A subject who has not received treatment with the therapeutic agent previously. |
| maintenance dose | An oral or IV dose, given following IV titration or loading, at regular intervals. |

Overview

Applicants have identified an accelerated dosing regimen for an antiarrhythmic drug allowing achievement of steady-state maximum plasma concentration (Cmax,ss) of the antiarrhythmic drug by intravenous and oral administration. The methods described herein may be used to titrate dosage for a particular patient based on their tolerability for the drug, whether the patient is naïve to the drug or whether the patient has stopped taking the drug for some time and a maintenance dose is to be re-initiated in the patient.

The methods described herein take into consideration the renal health of the patient, wherein dosages vary based on whether the patient has normal or abnormal renal health (renal impairment, for example).

The dosing regimen described in the method embodiments herein provides a titration of the drug in order to safely increase the dose of the drug to reach a target maintenance dose in a shorter period of time than the existing standard of care which includes a 3-day hospital stay to reach the target maintenance dose for a patient. Existing methods for achieving a target maintenance dose in a patient includes treating with oral (PO) sotalol, initiated at a dose of 80 mg twice daily, with gradual titration to 240 mg and 360 mg/day as needed.

In at least a first embodiment, a method according to the invention includes detecting a baseline QTc (corrected QT) level in a subject to receive treatment. In the method a first dose of an antiarrhythmic drug is administered by way of a first intravenous infusion for a first period of time. Following the first IV infusion, a first QTc measurement is taken, and a change from the baseline to the first QTc (a first delta QTc) is detected in order to determine whether it is safe to proceed with additional IV infusions to increase the dose of the drug for the subject. If the change in QTc from baseline is within an acceptable range, and it is determined safe to proceed, then a second dose of the drug is administered via a second IV infusion for a second duration of time. If it is not determined that it is safe to proceed, and the first delta QTc is outside an acceptable range, any further doses of the drug are administered orally, and the patient is monitored by a physician. Acceptable ranges for the first delta QTc include +/−20% from the baseline QTc measurement.

If following the second IV infusion, a second QTc measurement is taken, and the second delta QTc is in an acceptable range (+/−20% from the baseline QTc measurement), a third intravenous infusion dose of the drug is administered for a third duration of time. If the second delta QTc is not in an acceptable range, the patient is administered any further doses orally. An unacceptable delta QTc includes a value that is less than −20% from QTc baseline or greater than +20% from the baseline QTc. If at the end of the third intravenous infusion, the third delta QTc is acceptable (within +/−20% of the baseline QTc), any further doses of the drug may be administered orally, or alternatively, an additional intravenous infusion may be provided to the patient.

For patients suffering with abnormal renal function, the oral doses administered may be decreased, and/or the time between the intravenous dose and the oral dose or between subsequent oral maintenance doses may be lengthened. For example, the oral maintenance doses may be administered every 24 hours instead of every 12 hours for patients with renal impairment or abnormal renal function. In some instances, with patients having abnormal renal function, the IV doses administered may be decreased in amount or strength to account for any renal impairment.

DETAILED DESCRIPTION

FIG. 1A is a block diagram that illustrates an example normal ECG trace 120 for a single heartbeat, according to an embodiment. Time increases to the right and electric field strength increases vertically. The ECG trace 120 shows several labeled features including an initial increase P 101 in electric field followed in sequence by a dip Q 103, a spike R 105, another dip S 107 and a final increase T 109. Certain intervals are defined by these labeled features, including PR interval 121 from beginning of P 101 to beginning of Q 103, QRS complex from beginning of Q 103 to end of S 107, ST segment from end of S 107 to beginning of T 109, and QT interval from beginning of Q 103 to end of T 109. An RR interval refers to a time interval from the peak of R 105 to the peak of R in the next heartbeat, not shown. A rate corrected QT (abbreviated QTc) is given by the ratio of the QT interval to the square root of the RR interval. LQT occurs when the QT interval, or QTc, is substantively prolonged relative to normal variations.

The dosing method according to the current embodiment allows switching from IV to PO, and alternatively from one IV dosing to another IV dosing, such that the dosing method is configured to allow for substantial hospital cost savings and increased convenience.

Figure 12:
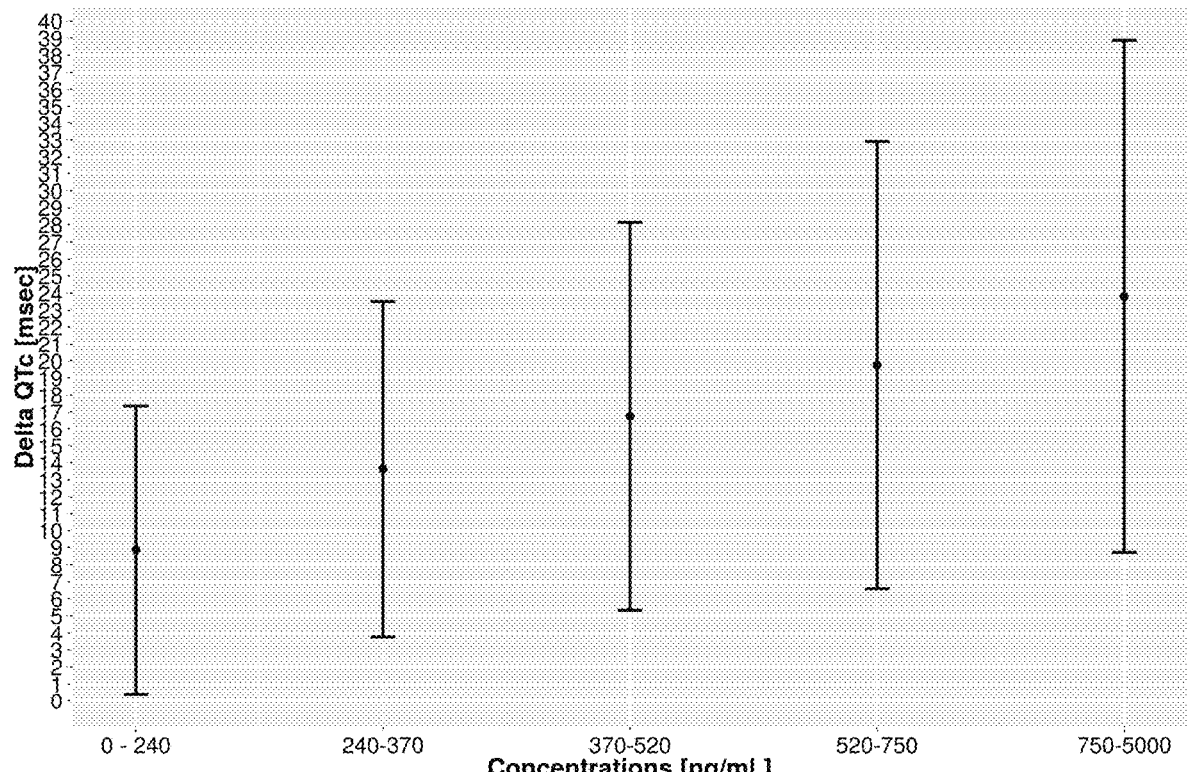
FIG. 12 is a graph illustrating multiple delta QTc profiles across concentrations observed after different titration designs.
Figure 13:
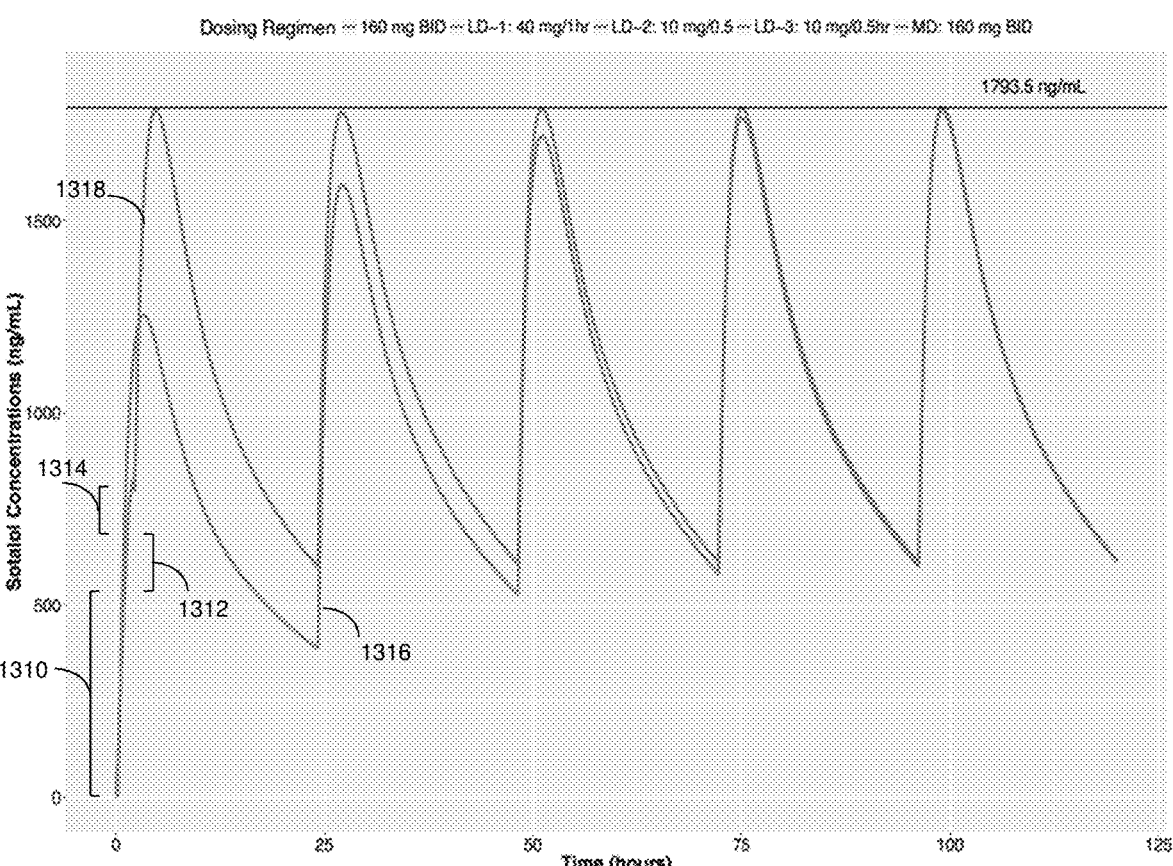
FIG. 13 is a graph illustrating a titration method embodiment for the 160 mg dose in a 70 kg patient with renal impairment.

The dosing methods described herein do not increase risk to a patient. This can be substantiated with the abundant literature on IV sotalol, in which IV infusions as rapid as 5 minutes were safely administered (Ho et al, 2004, 2005). Sotalol 1.5 mg/kg IV over 5 minutes is recommended by the ACLS guidelines in the treatment of stable-wide complex tachycardias in adult VT [Neumar 2010]. This recommendation was developed on the basis of various studies that evaluated the safety and efficacy of rapid infusions, reporting only mild to moderate adverse events, such as hypotension and dyspnea associated with the beta-blocking capabilities of sotalol [Jordaens 1991, Sung 1994], and QT prolongation [Nademanee 1985, Joardens 1991]. Further, a large meta-analysis of the risk of Torsades de Pointes in patients treated with rapid IV sotalol infusions showed minimal risk for patients treated with a single IV infusion of sotalol as compared to oral therapy [Marill 2011]. FIGS. 12 and 13 show that the risk of QTc prolongation is no more than 30 msec across all the doses in the proposed dosing regimens.

The dosing method according to one embodiment is generally applicable in patients with both normal or impaired renal function with a slight modification, as shown in FIGS. 5A, 6, and 7. The method and dosing regimens of the embodiments herein allow clinicians to cease infusions at any time if the QTc changes such that the QTc following any IV administration compared to the subject's baseline QTc is unacceptably prolonged. This flexibility is not available for an ingested tablet, for which three days of hospital monitoring is required to assess the QTc prolongation risk, resulting in increased cost of treatment.

Pharmacokinetic Model

FIG. 1B is a chart showing a pharmacokinetic (PK) model including an adjustment with data from both treatment arms for a reduced total administered dose of 62 mg. A 2-compartment model using first order absorption (with lag time) and elimination following IV and PO administration for fitted sotalol is shown in FIG. 1B. The relative bioavailability of IV to PO sotalol was also evaluated.

Figure 2:
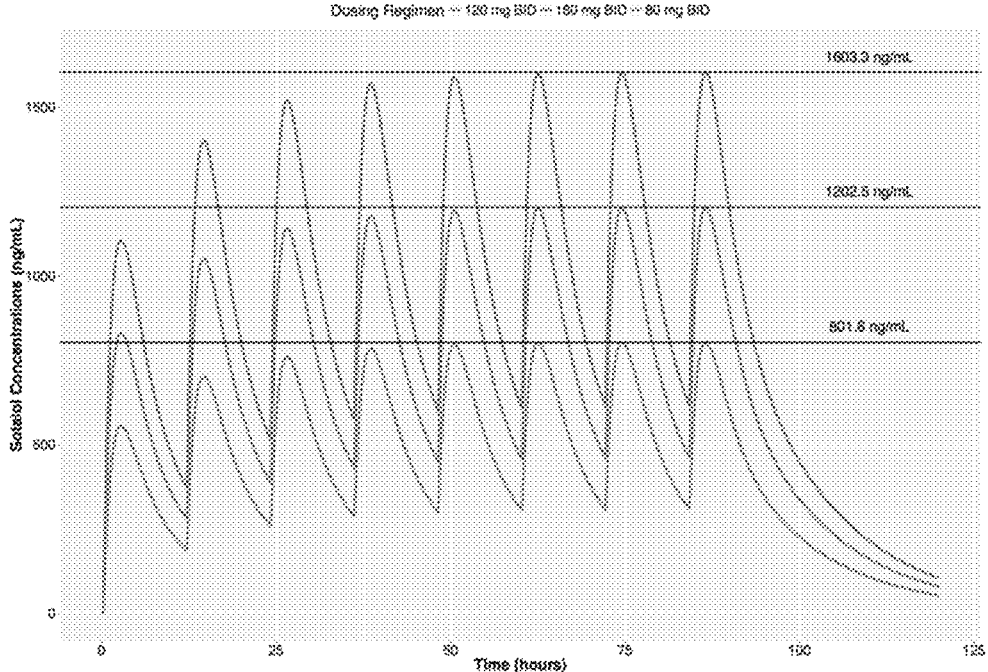
FIG. 2 is a graph illustrating the sotalol plasma concentrations approaching a steady state over many doses with the reference FDA recommended sotalol dosing regimens of 80, 120 and 160 mg BID given to a 70 kg patient.

FIG. 2 is a graph illustrating the sotalol plasma concentrations approaching a steady state over many doses with the reference FDA recommended sotalol dosing regimens of 80, 120 and 160 mg BID given to a 70 kg patient. The 80 mg BID dose is show by the bottom line in the graph, the 120 mg BID dose is shown by the middle line in the graph, and the 160 mg BID dose is shown by the top line in the graph.

Figure 3:
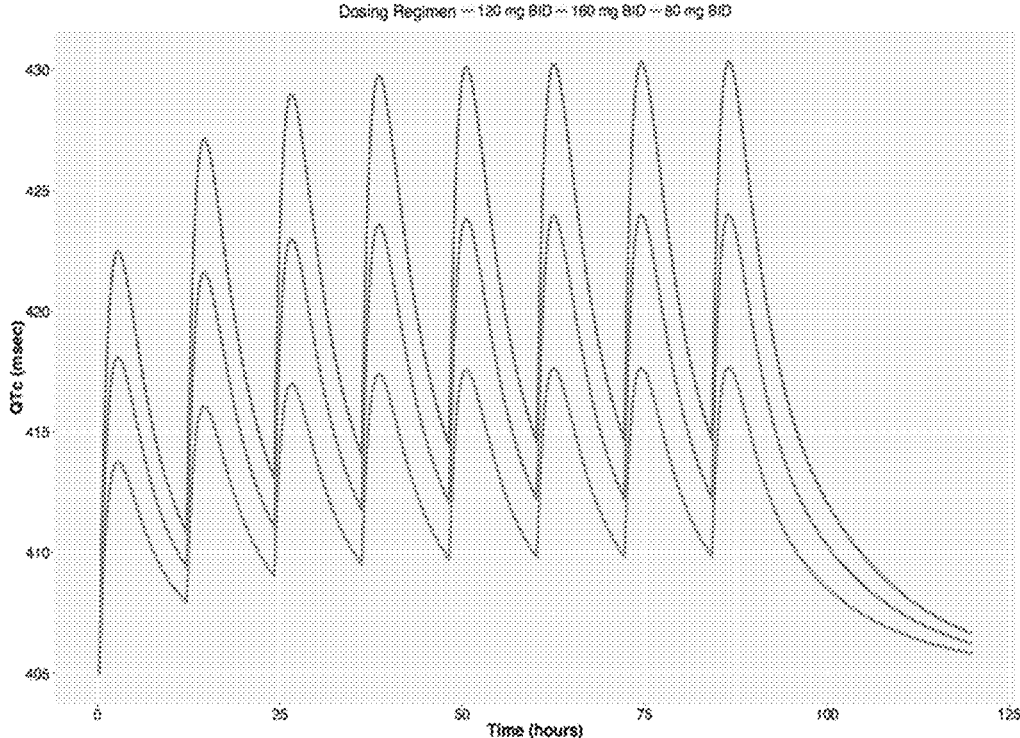
FIG. 3 is a graph illustrating a set of QTc profiles at these dose levels of FIG. 2 based on the concentration-QTc relationship.

FIG. 3 is a graph illustrating a set of QTc profiles at the dose levels shown in FIG. 2 based on the concentration-QTc relationship. The 80 mg BID dose is show by the bottom line in the graph, the 120 mg BID dose is shown by the middle line in the graph, and the 160 mg BID dose is shown by the top line in the graph.

Figures 4, 5:
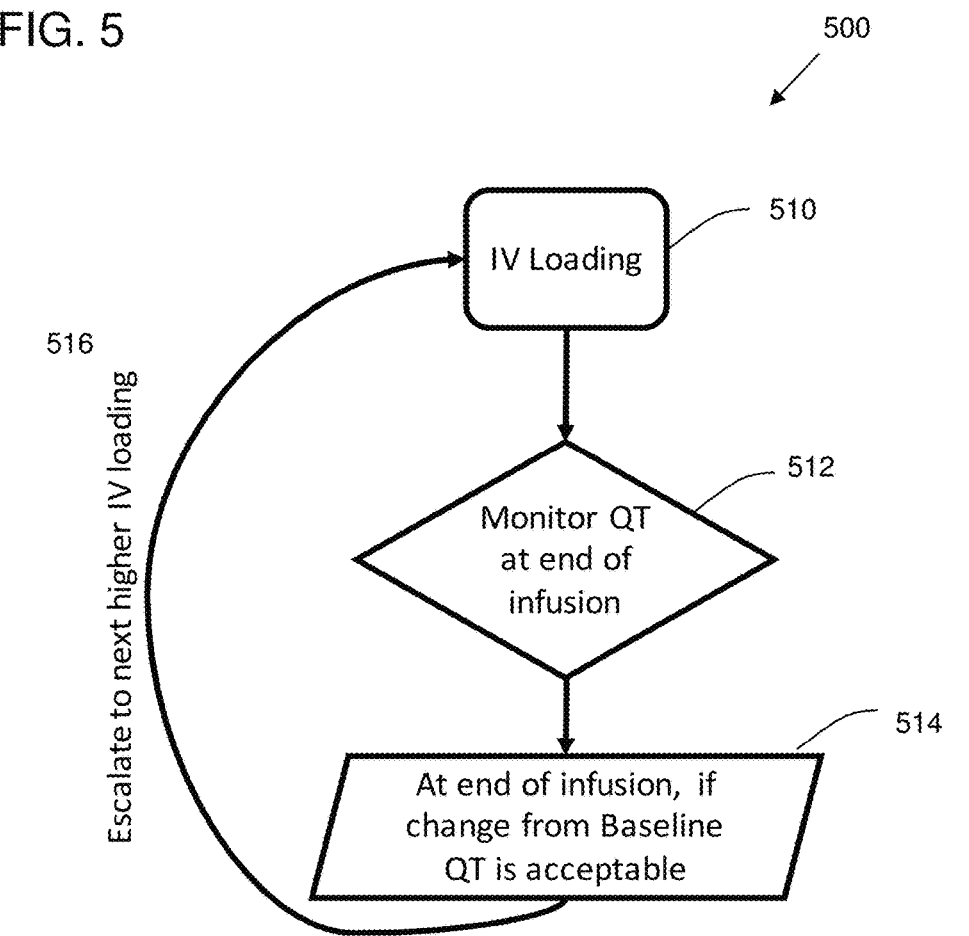
FIG. 4 is a table of dosing strategies explored for IV-oral switch.
FIG. 5 is a flow chart illustrating a dose titration scheme to initiate sotalol in naïve patients, according to one embodiment of the present invention.

FIG. 4 is a table of dosing strategies explored for IV-oral switch, for sotalol naïve patients as described in the methods for dosing herein.

FIG. 5 is a flow chart 500 illustrating a brief overview of a method for dosing an antiarrhythmic drug to initiate sotalol in sotalol-naïve patients, according to one embodiment. Initiation of the treatment includes titrating by IV loading 510, including, for example, by measuring a baseline QTc and then initiating a first dose administration of an antiarrhythmic drug by a first intravenous infusion for a first period of time. At the end of the IV infusion, a QTc measurement is taken, and is compared with the baseline QTc. If the change in QTc is within an acceptable range 514, a second dose of the drug is administered by IV infusion for a second period of time 516. Once the target maintenance dose has been reached, or, once the change in QTc measurement is found not to be within acceptable range, all IV infusions are discontinued, and the patient may further be administered oral doses of the drug only. Thus, the method includes titrating IV drug to allow safe dose escalation to the target oral maintenance dose, based on change from baseline in observed QT to the end of infusion (FIG. 5).

Effect of Sotalol Concentration on QTc

One embodiment of the method includes determining the change in QTc prolongation due to sotalol (e.g., sotalol-induced QTc prolongation) compared to the measured baseline QTc. QT prolongation risk is based on the relationship (e.g., provided in an FDA clinical pharmacology review) in which QTc=Baseline QTc+Slope×Concentration for Betapace tablets. Sotalol plasma concentration directly relates to QTc prolongation. Thus, one measure for evaluating safety of the method is QTc prolongation.

The method includes determining and recording a Baseline QTc prior to sotalol treatment, such as immediately prior to sotalol treatment. Concentration generally refers to observed sotalol plasma concentrations after initiation of the method, and Slope is generally a unit increase in QTc from Baseline QTc for a unit change in sotalol concentration. For example, the method of one embodiment determines Slope when determining the change of the QT interval from the baseline QTc. As a further example, Median Baseline QTc reported in clinical trials was 405 msec and the slope of the concentration QTc relationship was 0.0158 msec/ng/mL.

Dose Optimization

The method embodiments described herein are configured to optimize the dose and route of an antiarrhythmic drug to reduce the hospital length of stay by accelerating Cmax,ss to earlier times, e.g., on Day 1, without compromising the patient's safety. The method according to current embodiment is further configured to:

a. Define an IV loading dose and oral maintenance strategy to re-stabilize patients who were on prior stable PO sotalol therapy; and b. Define an IV dose titration scheme for sotalol-naïve patients to enable selection of a stable oral maintenance dose.

Dose Re-Stabilization Method

Generally, patients who are temporarily discontinued from oral sotalol therapy, either due to surgery or other reasons, need to be re-stabilized to their Cmax,ss as soon as possible. Re-initiation typically involves approximately 3 hospital days of monitored oral drug administration of the antiarrhythmic drug before the target dose Cmax, ss is achieved. FIG. 2 provides the average Cmax,ss on Day 3 for patients with normal renal function, based on the reference PO dose. Specifically, FIG. 2 shows the recommended sotalol dosing regimens of 80, 120 and 160 mg BID given to a 70 kg patient a) as sotalol plasma concentrations approach steady-state after 5-6 doses; and b) for QTc profiles at these dose levels based on the concentration-QTc relationship, as shown in FIG. 3.

Dose Titration for Sotalol Naïve Patients

According to one embodiment of the method, initiating the treatment includes titrating sotalol. Additional embodiments can further include applying the IV loading strategy having progressively higher titrating doses, such as higher doses of 120 or 160 mg (e.g., target oral maintenance doses), based on tolerability. Thus, the method includes titrating IV sotalol to allow safe dose escalation to the target oral or IV maintenance dose, based on change from baseline QTc compared to the QTc measured at the end of a given IV infusion (FIG. 5).

QTc Monitoring

According to another embodiment, the method includes determining the IV loading strategy according to a pharmacokinetic model, which describes a relationship between sotalol concentration and QTc prolongation. The method for both the re-stabilization and solatol-naïve patients (e.g., titration) embodiments uses the methods as discussed herein, in which the initial sotalol IV infusion ideally does not prolong QTc beyond a clinically acceptable range (e.g., >500 msec). Thus, the method can increase the likelihood that the calculated plasma concentrations are safe and do not exceed Cmax,ss for each dose level. After each IV infusion, QTc is measured and evaluated as being acceptable before a follow-up IV infusion is administered. If the QTc after an infusion is in an unacceptable range, then the protocol is changed so that no subsequent IV infusions are administered, and instead the protocol switches to oral administration of a known safe dose of the drug, Calculating the change in QTc across the range of doses can include determining and assuming variability between subjects in terms of pharmacokinetic parameters of the pharmacokinetic model and the concentration-QTc relationship.

Figure 9:
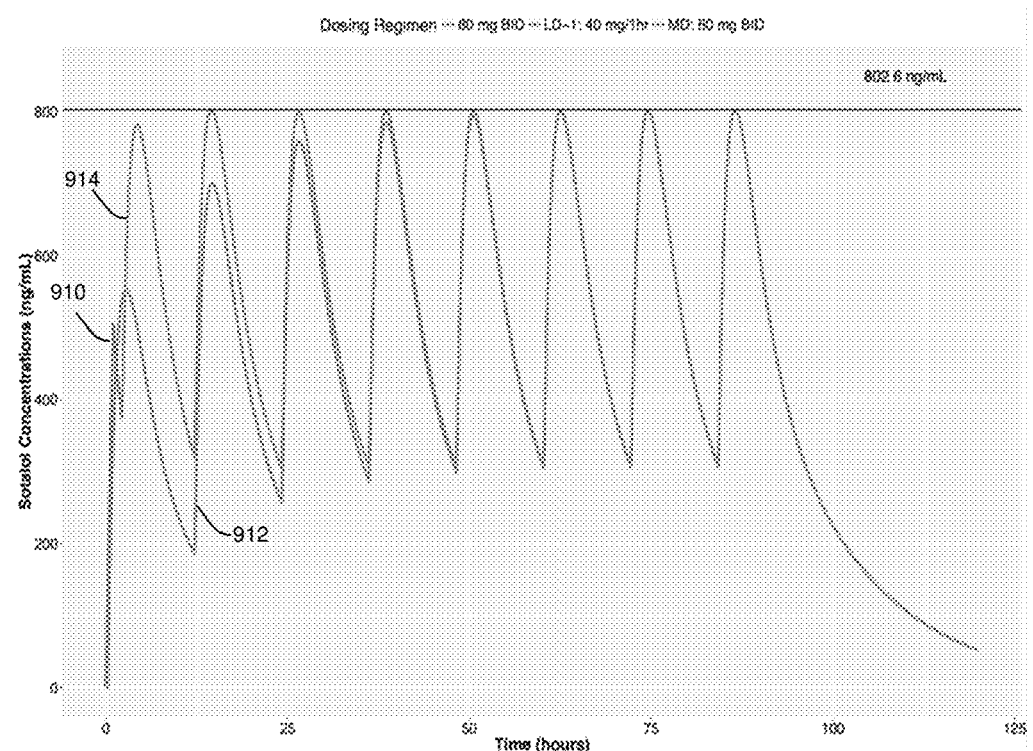
FIG. 9 is a graph illustrating a proposed titration method embodiment for the 80 mg dose.
Figure 10:
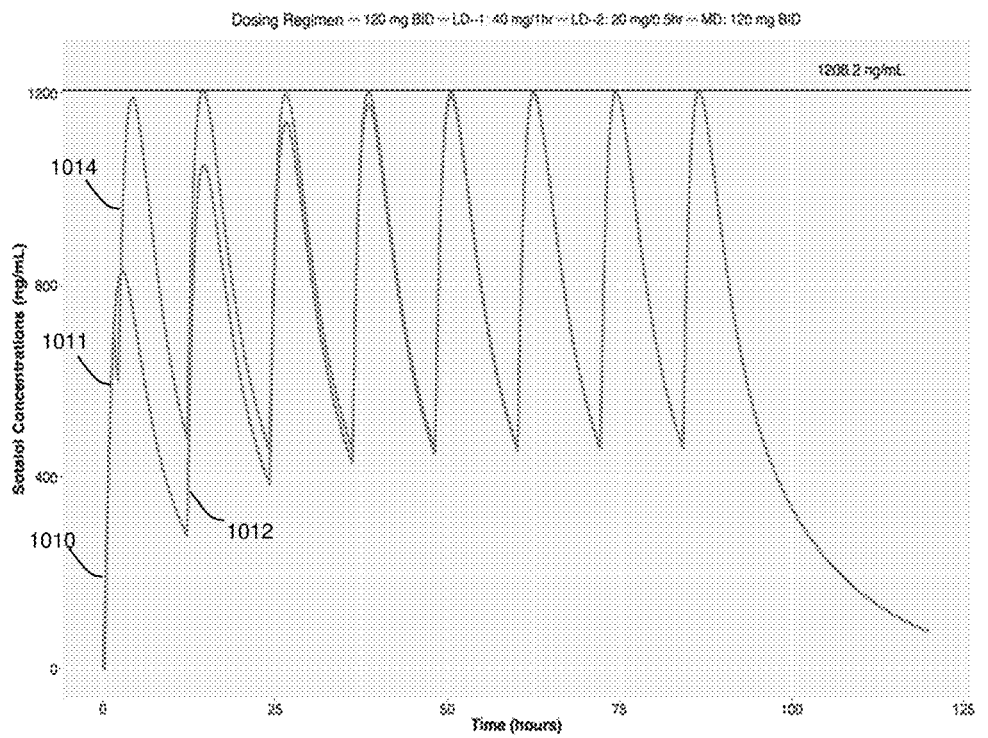
FIG. 10 is a graph illustrating a proposed titration method embodiment for the 120 mg dose.
Figure 11:
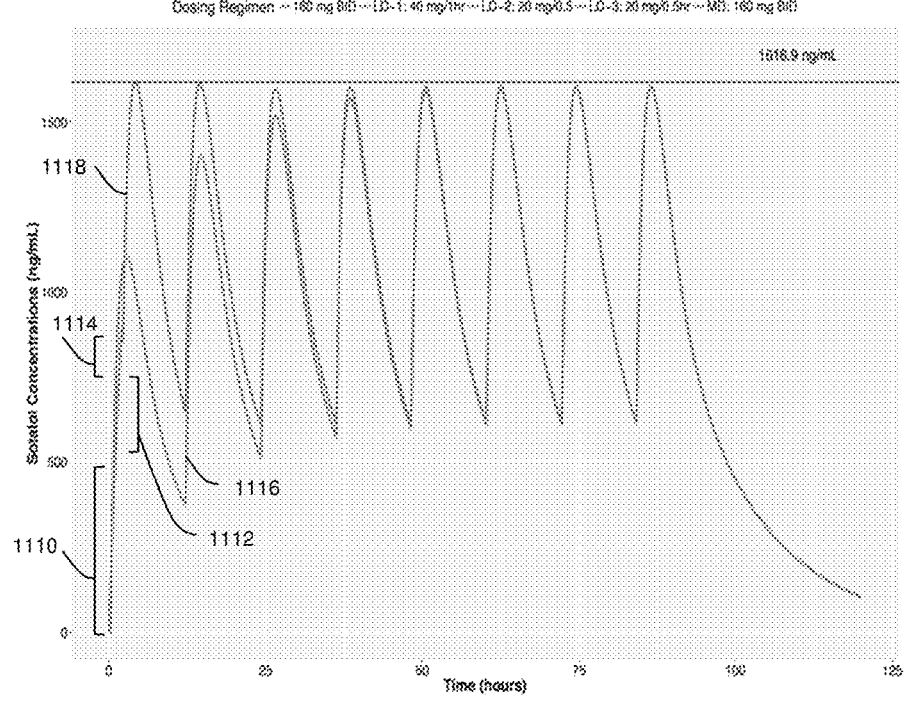
FIG. 11 is a graph illustrating a proposed titration design embodiment for the 160 mg dose.

FIGS. 9, 10, 11 are graphical illustrations of proposed titration designs for the 80, 120, and 160 mg doses.

Dose Adjustments for Patients with Renal Impairment

The product label recommends once-a-day dosing in patients with mild renal impairment (CLcr between 40 and 60 mL/min), and sotalol is contraindicated in patients with moderate to severe renal impairment (CLcr<40 mL/min). The inventors herein evaluated once-a-day dosing regimens that would facilitate earlier Cmax,ss in mildly impaired patients by assuming that sotalol clearance is 50% (6 L/hr) of the value observed in patients with normal renal function.

Reference Dose Comparison

The inventors evaluated the performance of the optimized dosing strategies by comparing the proposed computer simulated dosing scenario strategy to the reference dosing currently used in clinical practice which is the oral administration of 80, 120 or 160 mg BID.

Analyses

Evaluating dosing scenarios according to the current embodiment included simulation calculations. For example, for a re-stabilization embodiment, evaluating dosing scenarios included applying average pharmacokinetic parameters for a 70 kg patient (FIG. 2) in simulations using NONMEM (version 7.3; ICON, Ellicott City, MD). Post-processing of results were performed with R (https://www.r-project.org/). Evaluating dosing scenarios further included administering an initial IV loading dose based on labeled dose-titration rrecommendations. Thus, evaluating included using Monte Carlo simulations in 1,000 patients with a mean (SD) body weight of 70 kg. The variability in body weight and the random variability between subjects allowed the calculation of QTc prolongation for a range of sotalol concentrations. Quantitative metrics and graphs of time course of plasma sotalol concentrations, or the change in QTc, were used to compare the various dosing scenarios tested with the reference dosing, with a goal of ensuring that Cmax,ss was not exceeded, and with minimal risk of QTc prolongation.

Sotalol Pharmacokinetics

The results of evaluating the dosing scenarios according to a current embodiment indicated that the mean terminal half-life (t½) of sotalol is 12 hours in adults, and it takes about 2.5 to 3 days to achieve steady-state plasma concentrations. FIG. 1 shows the pharmacokinetic model parameters published in the FDA clinical pharmacology review used to develop the dosing method embodiments described herein. Based on these parameters, it takes about 5-6 oral doses, administered twice a day to reach Cmax,ss in a 70 kg subject with normal renal function.

Sotalol Concentration—QTc Relationship

As described above, the current embodiments of the method uses the FDA's linear function equation as a pharmacokinetic-QTc model to assess the relationship between sotalol concentration and QT prolongation. For example, the linear function equation uses the three reference BID PO doses (80, 120 and 160 mg) for a 70 kg individual with normal renal function and baseline QT of <405 msec. The concentrations determined by the pharmacokinetic model were those that produced an acceptable prolongation in the QTc measured after IV administration of not more than approximately 25 msec compared to the baseline QTc.

Dose Optimization

Optimizing the dosing method for a current embodiment is further configured to accelerate dosing of Cmax,ss to as early as Day 1 (FIGS. 9-11). For example, by optimizing the dosing method further included determining the average Cmax,ss and QTc prolongation at three different reference doses of 80 mg (FIG. 9), 120 mg (FIG. 10) and 160 mg (FIG. 11), administered intravenously as described below. The titration method embodiments shown in FIGS. 9-11 provide titration doses for 80 mg, 120 mg, and 160 mg doses as described, and demonstrate Sotalol concentrations in ng/mL during dosing. LD refers to a loading dose, and MD refers to a maintenance dose. The data of FIG. 9 shows a loading dose of Sotalol in the form of a 40 mg infused intravenous dose 910, wherein Sotalol concentrations reach approximately 500 ng/ml following the 40 mg Sotalol IV dose. The 40 mg IV dose is followed by an 80 mg PO Sotalol dose 912, further escalating Sotalol concentration every 12 hours as shown in FIG. 9. Finally, the 80 mg maintenance dose 914 is shown in FIG. 9, as provided every 12 hours thereafter, such that the Sotalol concentration in the patient reaches approximately 800 ng/mL approximately every 12 hours (BID) based on the maintenance dose.

FIG. 10 shows a loading dose in the form of a 40 mg Sotalol IV infusion for one hour 1010, and a 20 mg Sotalol IV infusion over 0.5 hours 1011 increasing the Sotalol concentration to nearly 800 ng/mL as shown. Following IV infusion, an oral dose (or in some embodiments this dose may be delivered by a further IV infusion) of 120 mg Sotalol is administered 1012, further increasing the concentration of Sotalol as shown. Finally, a maintenance dose of 120 mg Sotalol twice daily is delivered increasing Sotalol concentrations to approximately 1200 ng/mL as provided.

FIG. 11 shows Sotalol concentrations resulting from a first IV infusion of 40 mg Sotalol for one hour 1110 followed by a second IV infusion of 20 mg Sotalol for 0.5 hour 1112, followed by a third IV infusion of 20 mg Sotalol infused over 0.5 hour 1114. Thereafter, a 160 mg dose of Sotalol is administered 1116, in some embodiments PO such that the Sotalol concentration is shown to increase to over 1000 ng/mL Sotalol after the first 160 mg dose. Thereafter, a maintenance dose 1118 of 160 mg twice daily as otherwise described herein results in a Sotalol concentration of approximately 1616.9 ng/mL in a patient.

FIG. 13 demonstrates Sotalol concentrations during IV loading (ng/mL), wherein a first loading dose of 40 mg IV is infused over one hour 1310, a second dose of 10 mg IV is infused over 0.5 hours 1312, and a third loading dose of 10 mg IV is infused over 0.5 hours. Thereafter, a dose of Sotalol of 160 mg is delivered 1316 either PO or IV, and a maintenance dose of 160 mg is delivered 1318 PO or IV twice daily to maintain Sotalol concentrations at or above approximately 1600 ng/mL. The graphical data shows increases in the Sotalol concentration during IV loading as described in one embodiment of a method herein.

Re-Stabilization Method

In one embodiment, an optimal dosing regimen(s) achieved Cmax,ss as early as 4 hours after initiation of treatment on Day 1 (e.g., as described in FIG. 6).

In one example, a patient was stabilized on an 80 mg PO BID dose before interrupting the treatment. To achieve Cmax,ss for a 80 mg BID PO maintenance dose, the patient was first administered a dose of 40 mg IV sotalol infused over 2 hours. At the end of the two-hour infusion, the patient was administered an 80 mg dose by oral administration. A second PO dose of 80 mg was then administered 12 hours after the initiation of the first IV infusion, as recommended. Switching to the maintenance 80 mg PO dose at the end of the first infusion resulted in Cmax,ss concentrations of ~800 ng/mL at Tmax (2 hours) of the PO dose, approximately 4 hours after the initiation of approximately 25 msec first IV infusion. This indicates that Cmax,ss, which is typically reached within 3-5 days using the traditional oral loading protocol, can now likely be achieved within approximately 4 hours after initiation of a first IV loading infusion. Similar results were observed for the 120 and 160 mg oral BID doses.

FIG. 7 is a table according to one embodiment providing a schedule for dosing a patient with an antiarrhythmic drug. To achieve Cmax,ss equivalent to 75 mg IV sotalol infused over 5 hours, the patient is administered a first 40 mg IV infusion over 2 hours, and a second 5 hour infusion of 75 mg soon after completion of the IV loading dose (also herein the first IV dose), in one embodiment as shown in FIG. 7. In some examples described herein, the methods include administration of the drug by both IV and PO, or by multiple IV administrations. In some embodiments Cmax,ss is achieved within 4 hours of initiation of treatment in a method wherein one or more IV infusions are followed by oral administration, also called a mixed dosing method, In other embodiments, Cmax,ss is achieved within 7-14 hours after initiation of the first IV followed by one or more subsequent IV infusions.

Dose Titration for Sotalol Naïve Patients

FIG. 8 further describes a dose titration scheme of the current embodiment for initiating new sotalol patients. The dose titration scheme for initiating new sotalol patients includes analysis of many dosing scenarios (e.g., FIG. 4) and further includes a dosing regimen that is generally optimized for patients that require re-stabilization (FIG. 6). To reach Cmax,ss earlier, the method includes applying an IV loading strategy, after a baseline QTc is measured. The IV loading strategy begins with administering a first 40 mg IV loading dose for 1 hour, at which time the patient can be transitioned to 80 mg oral sotalol if an 80 mg BID oral maintenance dose is desired.

However, if the desired stable oral dose is 120 mg, then more than one IV infusion is used, and the QTc is measured after each infusion and compared to the baseline QTc to determine if it is safe to proceed. If the change in QTc from baseline is within an acceptable range, the titration may proceed by moving to the next IV infusion. In one embodiment, wherein the subject has normal renal function, an additional (second) 20 mg IV is administered over 0.5 hours. The dose titration scheme for initiating new sotalol patients can further include measuring the QTc interval and if it is in an acceptable range, determining that a third 20 mg IV infusion for 0.5 hour may be given for those patients with normal renal function to increase sotalol concentration; after which the method permits a switch to 160 mg sotalol PO. After the 3rd QTc measurement, for example, the dose can be any of 80, 120 or 160 mg PO or the equivalent IV in some embodiments.

In some embodiments, QTc will be measured at the end of every 0.5 hour (or when the infusion is finished). The measurement of QTc is a quick procedure, therefore, the subsequent infusion following QTc measurement is administered after the QTc reading is taken. In some embodiments, the IV infusion will still be connected to the patient, but the infusion may be stopped during the QTc measurement.

If the QTc is measured, and is found to be not within an acceptable range, no further IV administration is undertaken, and either an oral maintenance dose of 160 mg sotalol is maintained, or the patient may be de-escalated to 120 mg maintenance dose twice daily or possibly 80 mg maintenance dose, twice a day by oral administration. The oral maintenance doses described herein may be initiated either 1) 12 hours from the initiation of the first IV infusion, or 12 hours from the completion of the first IV infusion for patients with normal renal function, or 2) 24 hours from initiation of the first IV infusion, or 24 hours from the completion of the first IV infusion for patient with abnormal renal function.

Thus, titration-based dosing according to method embodiments described herein, is in accordance with the FDA guidelines and provides clinicians additional dosing control and flexibility during treatment because IV infusion occurs in multiple steps or stages that can be interrupted and switched to oral administration at any point if the patient is unable to tolerate the infusion.

Evaluation of QT Interval Prolongation

While ensuring sotalol concentrations did not exceed Cmax,ss relative to the reference PO doses, QT interval prolongation was also evaluated. FIG. 12 shows the change in QTc from baseline across a range of concentrations observed during the IV/PO switch across all three doses 80, 120 and 160 mg. The maximum change in QTc observed at the highest concentration is approximately 30 msec, a clinically acceptable range considering sotalol prolongs the QT interval as a general property of the drug class.

Dosing in Renally Impaired Patients

As was described above, embodiments describe methods of dosing sotalol for patients being re-stabilized on oral sotalol therapy, or alternatively, dosing sotalol for sotalol—naïve patients (see FIGS. 6, and 7). Methods are provided for dosing sotalol for renally impaired patients, which methods are generally similar to the embodiments described above for patients with normal renal function. Dosing sotalol for renally impaired patients includes maintenance PO doses given once-a-day in accordance with the product label, and reducing by half the amount of sotalol administered after the initial IV infusion. Thus, some embodiments described herein allow the Cmax,ss to approximately match concentrations achieved at steady-state after BID PO dosing in normal patients (see FIG. 13).

Antiarrhythmic Drugs

The term "antiarrhythmic drug" as used herein, includes, sotalol, dofetilide, flecainide, propafenone, amiodarone, dronedarone, or ibutilide among other antiarrhythmic drug known in the art. Other classes of drugs may also be used with the methods described herein, wherein there is an availability of an IV and oral formulation of the drug, and minimal to no risk to the patient by loading the patient on a larger IV dose. Sotalol (Betapace) for oral administration is available as a generic tablet from Covis Pharma By, UPsher Smith Labs, Apotex Inc., among other manufacturers. Sotalol for IV administration is available at Altathera Pharmaceuticals.

As described herein the antiarrhythmic drugs of the some embodiments are administered preferably either orally, preferably as solid compositions, or intravenously as a liquid composition. However, the drugs may be administered parenterally, by inhalation spray, topically, rectally, nasally, buccally, vaginally or via an implanted reservoir. Sterile injectable forms of the therapeutic agents may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The antiarrhythmic drugs employed in some embodiments may be orally administered in any orally acceptable dosage form, including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The antiarrhythmic drugs employed in the some embodiments may also be administered by nasal aerosol or inhalation. Such antiarrhythmic drugs may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the composition into creams, ointments, or transdermal patches.

The passage of agents through the blood-brain barrier to the brain is not desired but can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier. The passage of the agent can also be facilitated by its covalent coupling to a peptide vector capable of transporting the agent through the blood-brain barrier. Peptide transport vectors known as blood-brain barrier permeabilizer compounds are disclosed in U.S. Pat. No. 5,268,164. Site specific macromolecules with lipophilic characteristics useful for delivery to the brain are disclosed in U.S. Pat. No. 6,005,004.

Examples of routes of administration comprise oral, parenteral, e.g., intravenous, intradermal, subcutaneous, inhalation, transdermal (topical), transmucosal, and rectal administration. Solutions or suspensions used for parenteral, intradermal, or subcutaneous application can comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

The parenteral preparation can be enclosed in ampoules, disposable syringes or multiple dose vials made of glass or plastic. Therapeutic agents suitable for injection comprise sterile aqueous solutions (where water soluble) or dispersions and sterile powders for the extemporaneous preparation of sterile injectable solutions or dispersions. For intravenous administration, suitable carriers comprise physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof.

The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as manitol, sorbitol, or sodium chloride. Prolonged absorption of an injectable composition can be achieved by including in the composition an agent that delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the methods of preparation comprise vacuum drying and freeze-drying which yields a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and comprise, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The antiarrhythmic drugs may also be prepared in the form of suppositories (e.g., with conventional suppository bases such as cocoa butter and other glycerides) or retention enemas for rectal delivery.

Alternatives and Extensions

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

The invention claimed is:

1. A method comprising, in the following order:
(a) detecting a baseline QTc of a subject;
(b) administering a dose of a class III antiarrhythmic drug to the subject via a first intravenous infusion for a first duration of time;
(c) detecting a second QTc of the subject and determining a delta QTc from the difference between the second QTc measured after the first intravenous infusion and the baseline QTc; and
(d) determining whether the delta QTc is or is not within a specified range;
wherein if the delta QTc is within the specified range then (e) administering a further dose of the class III antiarrhythmic drug to the subject via a second intravenous infusion for a second duration of time, or administering at least one oral dose of the class III antiarrhythmic drug to the subject; or wherein if the delta QTc is not within the specified range then (e) discontinuing the first intravenous administration and administering any further doses of the class III antiarrhythmic drug to the subject as an oral dose or doses, or administering a reduced second intravenous dose or doses to the subject.

2. The method of claim 1, wherein the class III antiarrhythmic drug is sotalol.

3. The method of claim 1, wherein the class III antiarrhythmic drug is dofetilide.

4. The method of claim 2, wherein the class III antiarrhythmic drug is amiodarone.

5. The method of claim 1, wherein the duration of time is 0.5 hour-2 hours.

6. The method of claim 1, wherein the subject has normal or abnormal renal function and the dose of class III antiarrhythmic drug administered via the intravenous infusion is 10 mg-80 mg.

7. The method of claim 1, wherein the subject has normal or abnormal renal function, and wherein the at least one oral dose of the class III antiarrhythmic drug comprises 80 mg, 120 mg, or 160 mg.

8. The method of claim 1, wherein the subject has normal renal function and at least one of the oral dose(s) of the class III antiarrhythmic drug is administered at a 12-hour interval from a previous oral dose.

9. The method of claim 1, wherein the subject has abnormal renal function and at least one of the oral dose(s) of the class III antiarrhythmic drug is administered at a 24-hour interval from a previous oral dose.

10. A method comprising, in the following order:
(a) detecting a baseline QTc of a subject;
(b) administering a dose of a class III antiarrhythmic drug to the subject via a first intravenous infusion for a first duration of time;
(c) detecting a second QTc of the subject;
wherein if the second QTc of the subject prolongs to >500 msec, then (d) discontinuing the first intravenous administration and administering any further doses of the class III antiarrhythmic drug to the subject as an oral dose or doses, or administering a reduced second intravenous dose or doses to the subject; or
wherein if the further QTc does not prolong to >500 msec, then (d) administering at least one oral dose of the class III antiarrhythmic drug to the subject, or administering a second intravenous infusion to the subject for a second duration of time.

11. The method of claim 10, wherein the class III antiarrhythmic drug is sotalol.

12. The method of claim 10, wherein the class III antiarrhythmic is dofetilide.

13. The method of claim 10, wherein the class III antiarrhythmic is amiodarone.

14. The method of claim 10, wherein the subject has normal or abnormal renal function and the dose of class III antiarrhythmic drug administered via the intravenous infusion is 10 mg-80 mg.

15. The method of claim 10, wherein the subject has normal renal function and at least one of the oral dose(s) of the class III antiarrhythmic drug comprises 80 mg, 120 mg, or 160 mg.

16. The method of claim 10, wherein the subject has abnormal renal function and at least one of the oral dose(s) of the class III antiarrhythmic drug comprises 80 mg, 120 mg, or 160 mg.

16

17. A method comprising, in the following order:
(a) detecting a QTc of a subject;
(b) administering a dose of a class III antiarrhythmic drug to the subject via a first intravenous infusion for a first duration of time;
(c) detecting a second QTc of the subject;
wherein if the further QTc of the subject prolongs to >500 msec, then (d) discontinuing the first intravenous administration and administering any further doses of the class III antiarrhythmic drug to the subject as an oral dose or doses or administering a reduced second intravenous dose or doses to the subject; or
wherein if the further QTc does not prolong to >500 msec, then (d) administering at least one oral dose of the class III antiarrhythmic drug to the subject or administering a second intravenous infusion to the subject for a second duration of time, wherein the subject achieves steady-state maximum plasma concentration within about 24 hours after initiation of administering the first intravenous infusion.

18. The method of claim 17, wherein the class III antiarrhythmic drug is sotalol.

19. The method of claim 17, wherein the class III antiarrhythmic drug is dofetilide.

20. The method of claim 17, wherein the class III antiarrhythmic drug is amiodarone.

21. The method of claim 17, wherein the dose of class III antiarrhythmic drug administered via the intravenous infusion is 10 mg-80 mg.

22. The method of claim 17, wherein the at least one oral dose of the class III antiarrhythmic drug is in an amount of 80 mg, 120 mg, or 160 mg.

23. The method of claim 22, wherein the at least one oral dose is administered at a 12-hour interval or at a 24-hour interval from a previous oral dose.

* * * * *